United States Patent [19]

Koblitz et al.

[11] Patent Number: 4,491,453

[45] Date of Patent: Jan. 1, 1985

[54] PROCESS FOR RESTORING TEETH WITH VISIBLE LIGHT CURABLE COMPOSITIONS

[75] Inventors: Francis F. Koblitz, York, Pa.; Roy L. Smith, Milford, Del.

[73] Assignee: Dentsply Research & Development Corp., Milford, Del.

[21] Appl. No.: 550,747

[22] Filed: Nov. 10, 1983

Related U.S. Application Data

[63] Continuation of Ser. No. 406,462, Aug. 9, 1982, abandoned, and a continuation-in-part of Ser. No. 323,313, Nov. 20, 1981, abandoned, which is a continuation of Ser. No. 182,626, Aug. 29, 1980, abandoned.

[51] Int. Cl.$^3$ .............................................. A61K 6/08
[52] U.S. Cl. .................................... 433/217; 433/199; 433/201; 433/202; 433/212; 433/222; 433/226; 433/228; 260/998.11; 523/115; 523/116; 523/117
[58] Field of Search ............... 433/168, 201, 202, 199, 433/226, 228, 212, 217; 260/998.11; 106/35; 523/115, 116, 117

[56] References Cited

U.S. PATENT DOCUMENTS

| | | | |
|---|---|---|---|
| 3,254,411 | 6/1966 | Shelley | 32/15 |
| 3,488,269 | 1/1970 | Allen et al. | 204/159.23 |
| 3,677,920 | 7/1972 | Kai et al. | 204/159.15 |
| 3,709,866 | 1/1973 | Waller | 260/27 R |
| 3,759,809 | 9/1973 | Carlick et al. | 204/159.23 |
| 3,825,518 | 7/1974 | Foster et al. | 260/42.52 |
| 3,864,133 | 2/1975 | Hisamatsu et al. | 96/115 P |
| 3,954,584 | 5/1976 | Miyata et al. | 204/159.23 |
| 3,968,181 | 7/1976 | Uzelmeier et al. | 260/837 R |
| 4,065,587 | 12/1977 | Ting | 427/54 |
| 4,071,424 | 1/1978 | Dart et al. | 204/159.15 |
| 4,077,859 | 3/1978 | Costanza et al. | 204/159.23 |
| 4,089,762 | 5/1978 | Frodsham | 204/159.15 |
| 4,089,763 | 5/1978 | Dart et al. | 204/159.23 |
| 4,153,776 | 5/1979 | Friedlander et al. | 528/49 |
| 4,227,979 | 10/1980 | Humke et al. | 204/159.16 |

FOREIGN PATENT DOCUMENTS 12535 6/1980 European Pat. Off. .

*Primary Examiner*—Lorenzo B. Hayes
*Attorney, Agent, or Firm*—Woodcock Washburn Kurtz Mackiewicz & Norris

[57] ABSTRACT

Process for restoring teeth with visible light curable compositions having improved color stability are provided. According to a preferred embodiment, visible light hardenable restorative materials are formulated from a major proportion of inorganic filler and a minor proportion of a resin component comprising a binder resin selected from the group of acrylated polyesters, acrylated polyesters reacted with an isocyanate, and hydroxyalkyl acrylic esters reacted with an isocyanate, polymerizable acrylic diluent monomer in an amount sufficient to control the viscosity of the resin component, and a photosensitizing system comprising of from about 0.05% to about 0.50% by weight of the restorative material of an alpha diketone together with an amine reducing agent. American Dental Association color stability standards are met by these compositions.

9 Claims, No Drawings

PROCESS FOR RESTORING TEETH WITH VISIBLE LIGHT CURABLE COMPOSITIONS

This is a continuation of application Ser. No. 406,462, filed Aug. 9, 1982, abandoned and a continuation-in-part of Ser. No. 323,313 filed Nov. 20, 1981 abandoned which is a continuation of Ser. No. 182,626 filed Aug. 29, 1980 abandoned.

BACKGROUND OF THE INVENTION

This invention provides composite dental restorative compositions which are curable by the action of visible light. More particularly, formulations are disclosed which maintain good color stability and other beneficial physical properties while having the ease of workability and safety attendant to light curable materials.

Dental restoratives should exhibit certain obligatory physical and chemical characteristics in order to be suitable for use in filling, repairing or replacing teeth. Thus, restorative materials should possess properties that closely match natural teeth with respect to structural properties such as cohesive strength, coefficient of thermal expansion and wearability. Also, aesthetic considerations such as color stability, refractive index, plaque repellency, polishability and opacity are important factors in determining whether a material is suitable for use as a dental restorative. In the past, numerous organic compositions have been tried in various mixtures and proportions in order to find satisfactory materials for use as dental composites or restoratives. These compositions have usually included some type of resin, which may either be preblended or mixed by the practitioner in the office, together with other materials such as pigments, catalysts, handling agents and opacifiers. For restorative use, it is generally necessary to employ materials which are "filled", that is, to which have been added amounts of inorganic, or in some cases, organic particulate material.

Composite or restorative materials should be distinguished from most film forming dental compositions. Such film forming dental materials provide resins containing minor or no substantial amounts of filler materials. They are frequently used as sealants, glazes, bonding agents, or adhesives and may be used to coat a prepared tooth cavity prior to filling, thereby sealing off the tooth material against cracks and leaks adjacent to the filling. Such unfilled compositions have different viscosity requirements from dental composite materials because low viscosities are needed in the sealant materials in order to have proper flow characteristics. By contrast, dental composite and restorative materials must have good forming characteristics so that they can be shaped to fit a cavity area or molded into place in order to repair chipped or damaged teeth. Furthermore, such restorative compositions must preferably be filled with inorganic materials in order to achieve satisfactory hardness and durability during service.

It will be appreciated by those skilled in the art that the use of photoactivated materials is to be preferred over the more traditional thermochemical catalyst or redox activated systems because of the increased work time allowed by the use of photoinitiated polymerization. In a two-component catalyst or redox system, work time is determined by the reaction time once the catalyst is added to the resin component. In a photocured system, the practitioner may take whatever time is necessary for forming or molding the dental restoration into formation and then effect extremely rapid curing by exposing the photocurable material to the appropriate wavelength of electromagnetic radiation. Accordingly, effective aesthetically pleasing photochemically hardenable dental restorative compositions, have long been desired by those skilled in the art.

Some prior art dental materials have utilized photoinitiators that are sensitive to ultraviolet light radiation. There are, however, certain technical limitations which are present in ultraviolet-activated dental composite or restorative systems. For example, tooth structure attenuates ultraviolet radiation sufficiently so that it is not practical to cure ultraviolet-activated dental composites where direct access to the dental composite by the ultraviolet source is interfered with by intervening portions of tooth structure. Such is the case in classical undercuts used for mechanical retention of dental restorations. Ultraviolet-cured systems also cannot accomplish good depths of cure; stepwise restoration is frequently required.

It has been found that visible light having wavelengths from about 4000 angstroms to about 5000 angstroms is attenuated to a lesser degree by tooth structure than is ultraviolet radiation. Accordingly, it has been proposed to employ such visible light as the source of activating energy in dental compositions. Many previous attempts to develop restorative formulations using visible light curing systems have resulted in failure; such previous compositions have failed to exhibit one or more of the serviceability characteristics necessary for dental restoratives. A principal shortcoming is a lack of color stability and concomitant lack of aesthetic acceptability of the resulting products. Such a lack of color stability is a major shortcoming. The American Dental Association, the International Standards Organization, and others have developed detailed requirements for color stability in direct filling resins. See, for example, A.D.A. Specification No. 27; J.A.D.A. Vol. 94, June 1977, pp. 1191–1194.

Accordingly, it is a principal object of this invention to provide compositions which are useful as dental restoratives. It is another object to provide such dental materials which exhibit improved color stability. Another object of this invention is to provide a one-component photocurable dental restorative system which is photocurable using visible light. A further object is to provide dental compositions which exhibit a rapid cure time but which exhibit good workability prior to curing. Yet another object is to provide photocurable dental restoratives which are curable without use of ultraviolet radiation. A still further object is to provide dental compositions which are effective with lesser amounts of photoinitiators. Still other objects will become apparent from the following description of the invention.

It is to be understood that the term "bisphenol A" is commonly used in the art to indicate the chemical compound, 2,2-bis(4-hydroxyphenyl)propane. It is also to be understood that the term "bis-GMA" is commonly used to indicate the chemical compound 2,2-bis[4-(2-hydroxy-3-methylacryloxypropoxy)phenyl]-propane, otherwise referred to as "diglycidyl methacrylate of bisphenol A."

U.S. Pat. No. 3,825,518 to Foster et al. teaches dental filling materials which comprise a mixture of inorganic filler and the reaction product of an organic diisocyanate with a hydroxyalkyl acrylate or methacrylate to give a filled urethane diacrylate. A peroxide catalyst and a polymerization activator are employed.

U.S. Pat. No. 3,254,411 to Shelley teaches the use of a polyurethane liner to form a coating in the area of tooth to be filled. This liner acts as a sealant to prevent seepage of food particles and bacteria behind the filling that is to be placed in the tooth.

U.S. Pat. No. 3,488,269 to Allen et al teaches the use of visible light induced dye-redox initiated polymerization of vinyl monomers such as methacrylates. The improved initiators used here are characterized as having labile hydrogen.

U.S. Pat. No. 3,864,133 to Hisamatsu et al discloses photopolymerizable compositions which comprise a compound containing an ethylenically unsaturated double bond and urethane linkage and containing a secondary amino radical, a tertiary amino radical or a urea linkage. These materials are hardenable in the optional presence of air without the addition of wax. The materials formed are used in coating applications such as in wood sealers.

U.S. Pat. No. 3,759,809 to Carlick et al describes radiation curable compositions that have at least one isocyanate-modified polyfunctional ester with a hydroxyl value of about 15 to 70 used in conjunction with a photoinitiator. Reduced toxicity of these compounds is also noted. The primary use of these compounds is in lithographic inks.

U.S. Pat. No. 3,954,584 to Miyata et al. teaches that certain photopolymerizable vinylurethane monomers are useful in the preparation of printing plates and reliefs. Actinic light having wavelengths of from 2000 to 5000 angstroms may be used depending on the species of the photosensitizers used. Photopolymerizable vinylurethane monomers are used in conjunction with a photo co-polymerizable ethylenically unsaturated liquid monomer and a photosensitizer with the vinylurethane monomer.

U.S. Pat. No. 4,065,587 to Ting utilizes UV curable poly(ether-urethane)polyacrylates for the formation of wet-look polymers. U.S. Pat. No. 3,968,181 to Uzelmeier teaches modified photocurable acrylate resins including bis-GMA. A UV sensitizer such as a benzoin ether may be employed. These materials are useful as coatings and adhesives. U.S. Pat. No. 4,153,776 to Friedlander et al discloses amide-modified urethane acrylate radiation curable compounds which are useful in film applications.

U.S. Pat. No. 4,071,424 to Dart et al. teaches a photopolymerizable composition comprising at least one ethylenically unsaturated material and a photosensitive catalyst. Preferred photosensitizing systems employ alpha diketones with an amine reducing agent capable of being excited by radiation in the visible as well as in the UV region or both.

U.S. Pat. No. 4,089,762 to Frodsham teaches the use of a photopolymerizable composition comprising a polymerizable ethylenically unsaturated material, a photosensitizer of the structure which is preferably a diketone and a N-alkyl or N-cycloalkyl morpholine.

U.S. Pat. No. 4,089,763 to Dart et al teaches a method of repairing teeth using a composition which is curable by irradiation with visible light. These compositions include isocyanate modified bisphenol A derivatives in conjunction with a visible light sensitizing system.

U.S. Pat. No. 3,709,866 to Waller, assigned to the assignee of this invention, discloses the hexamethylene diisocyanate adduct of bis-GMA in a UV photocurable system. Benzoin methyl ether is employed as a UV activator. This disclosure is in part reflected in the commercial products NUVA-FIL, and NUVA-FIL P.A., which are registered trademarks for products past or present of the L. D. Caulk Co.

U.S. Pat. Nos. 4,227,979 issued to Humke et. al., 3,625,744 issued to Juna et. al, and 4,077,859 issued to Costanza are each directed to radiation curable coating compositions.

British Pat. No. 569,974 issued to DuPont discloses photopolymerizable dental compositions comprising polymer-monomer mixtures. Dental restoratives having major proportions of inorganic fillers are not suggested thereby.

U.S. Pat. No. 4,292,029 issued to Craig et. al. is directed to hydrophobic dental composite restorations. The possibility of visible light curable one-phase systems is suggested.

None of the the foregoing disclose or suggest the novel methods and compositions of the present invention.

SUMMARY OF THE INVENTION

The present invention provides novel moldable dental restorative compositions hardenable by irradiation with visible light. Such compositions comprise a major proportion of inorganic filler and a minor proportion of a resin component. The resin component comprises a binder resin which includes either acrylated polyesters, acrylated polyesters reacted with an isocyanate, or a hydroxyalkyl acrylic ester reacted with an isocyanate. The binder resin is mixed with an amount of a polymerizable acrylic diluent monomer sufficient to dissolve the binder resin and to adjust the viscosity of the resin component to from about 5000 to about 70,000 centipoises at 25° C.

A photosensitizing system is also included in the resin component comprising from about 0.05% to about 0.50% of an alpha diketone together with an amount of an amine reducing agent sufficient to improve the photocatalytic activity to visible light of the alpha diketone in the restorative composition.

The relative amount of filler and resin components is selected such that the overall restorative composition has a viscosity suitable for the restoration of teeth. Unlike prior photocurable dental restoratives, those of the present invention are capable of passing American Dental Association specification number 27 for color stability.

Such dental compositions may comprise unitary or one-component blends of binder resins, diluent monomers, fillers and photoactivating or photosensitizing systems which are sensitive to visible light. Such compositions may optionally be modified through the addition of restorative modificants such as pigments, stabilizers, opacifiers, etc. These materials are freely workable under ambient conditions until they are exposed to visible light. At such time a rapid cure is effected to yield strong, durable, polishable dental restoratives with improved color stability.

DETAILED DESCRIPTION OF THE INVENTION

The compositions of this invention comprise visible light polymerizable, hardenable blends comprising fillers, binder resins, diluent monomers, and a visible light photosensitizing system. Such blends may optionally include pigments, opacifiers, handling agents and other modificants as will be appreciated by those skilled in the art.

Binder resins suitable for use in the practice of one or more of the embodiments of this invention include a wide variety of ethylenically unsaturated polymerizable compositions. Preferably, such resins are selected from the class of acrylated polyesters. Thus, the acrylic and methacrylic adducts with bisphenol-A glycidate monomers, dimers, trimers, etc. are preferred; most preferred is bis-GMA. Those skilled in the art will appreciate that other acrylated polyesters may also be suitable. Such acrylated polyesters may also be reacted with isocyanates to form urethanes useful as binder resins. Thus, bis-GMA may be reacted with a mono-or diisocyanate (or other isocyanate) such as hexamethylene diisocyanate, phenylene diisocyanate or a wide variety of other aliphatic and aromatic diisocyanates to provide useful binder resins. The adducts of bis-GMA with hexamethylene diisocyanate have been found to be the best binder resins presently known for use in this invention. Alternatively, the adducts of 2,2,3-trimethylhexane diisocyanate with hydroxyethyl methacrylate, hydroxypropyl methacrylate and other hydroxyalkyl species are also preferred.

A diluent monomer is added to the compositions of this invention in amounts sufficient to result in polymerizable resin components having viscosities between about 5,000 and about 70,000 centipoises, and preferably between about 15,000 and about 45,000 centipoises at 25° C. Other viscosities may be employed for certain embodiments, however. Such viscosity control will be understood by those skilled in the art to result in materials suitable for inclusion in a wide range of dental restoratives. Diluent monomers may be any of a wide range of polymerizable monomers capable of sustaining a photochemically initiated polymerization. More preferably, such diluents may be the di-, tri- and higher acrylic species such as ethylene glycol dimethacrylate, diethylene glycol dimethacrylate, triethylene glycol dimethacrylate, etc., trimethylol propane trimethacrylate, analogous acrylates, and similar species.

The photosensitizing system employed in the formulation of dental materials according to the practice of this invention comprises two components, an alpha diketone photosensitive species (also known as an alpha, beta diketone) and an amine reducing agent. While any alpha diketone which is capable of initiating polymerization in the polymerizable systems of this invention may be employed, camphoroquinone, benzil, biacetyl, 9,10-phenanthrenequinone, and naphthoquinone have been found to be preferred. Non-aromatic alpha diketones, especially camphoroquinone and biacetyl have been found to be the best photoinitiators for use in the practice of this invention. Such non-aromatic species are believed to be most useful in formulating restoratives which pass the A.D.A. color stability test. Most preferred is camphoroquinone.

The alpha diketone is combined with an amine reducing agent; the two taken together form the visible light sensitizing system useful for the practice of this invention. Numerous amines have been found to be useful as reducing agents for the alpha diketones used herein. Thus, amines such as tributylamine, tripropylamine are useful. Still more useful are substituted amines such as N-alkyldialkanolamines and trialkanolamine; N-methyldiethanolamine is most preferred. Those skilled in the art will appreciate that numerous other alpha diketones and amine reducing agents may be employed without deviating from the spirit of this invention.

The improved color stability of the dental restoratives according to this invention is believed to be at least in part of a result of the careful control of the amounts and identity of alpha diketone sensitizers employed therein. Accordingly, the amount of alpha diketone photosensitizer is controlled to comprise from about 0.05% to about 0.50% by weight based upon the total weight of the binder resin, diluent monomer and photosensitizing system. It is even more preferred to employ from about 0.10% to about 0.30% of alpha diketone and to use non-aromatic species such as camphoroquinone or biacetyl. The amount of amine reducing agent is less critical. It is useful to employ from about 0.2% to about 1.0% of amine with from about 0.3% to about 0.6% being preferred, based on the total weight of binder, diluent and photosensitizing system.

For the formulation of the visible light polymerizable compositions of this invention, the binder resin, diluent and visible light photosensitizing system are blended together with fillers and, optionally but preferably, pigments and modificants. Those skilled in the art will appreciate that the amount of filler loading which may be accomplished with a given resinous system will depend upon several variables including the identity of the resins and fillers and the particle sizes of the fillers. It must be appreciated that, for a given resin formulation, judicious choice of filler type and filler particle size must be made. The filler used must be such that the transmittance of visible light by the restorative compositions is sufficient for polymerization to take place. Those skilled in the art will be able to select fillers and to determine filler particle sizes based upon this requirement.

Among those fillers which are especially suited for use in the practice of this invention are inorganic glasses. Preferred among these are barium aluminum silicate, lithium aluminum silicate, strontium, lanthanum, tantalum, etc., glasses, and related materials. Silica, especially in submicron sizes, quartz, and other fillers may also be employed in some formulations. Such fillers are preferably silanated prior to use in the restoratives of this invention. Silanation is well known to those skilled in the art and any silanating compound known to them may be used for this purpose.

Fillers are selected having particle sizes which are, in general, less than about 50 microns. It is known that smaller sized filler particles result in highly polishable dental materials, but that the concomitant increase in surface area diminishes the overall filler loading possible with a given resin. Such lower loadings may be manifested by lesser degrees of strength, hardness, and durability in the resulting polymerized structures. It is possible to employ submicron sized fillers in some cases, however. The ratio of resin to filler employed for the practice of this invention must take account of the filler size as suggested above. In general, weight ratios of from about 10:90 to about 50:50 may be used, with from about 15:85 to about 30:70 being preferred.

Pigments, opacifiers, brightening agents, handling agents and other modificants may be included in the compositions of this invention without departing from its spirit.

While the components of the restorative composition may be added in any order, it has been found useful and convenient to mix the binder resin and diluent together, to add the photosensitizing system components, and then to blend in the filler together with pigments and other modifying agents. In practice, the binder resin and diluent are mixed together in a proportion such that the final polymerizable composition will have a viscosity suitable for dental restorative composites such as for the filling of teeth. While the relative amounts of binder resin and diluent will vary depending upon their identity and the type, size and amount of filler to be used, ratios of binder resin to diluent of from about 12:1 to about 1:2 and more preferably, of from about 6:1 to about 1:1 are generally employed.

The methods of use of the visible light curable compositions of this invention follow, to an extent, those currently practiced by those skilled in the art. Thus, the surface to be repaired is cleansed of decayed material and acid etched to promote bonding. At this point, a bonding agent may be employed by coating it upon the surface to be repaired. A material according to this invention is then molded into place in the conventional fashion. At this point, visible light is directed onto the restorative material by any suitable source. One such source is described in the application of Gonser "Visible Light Apparatus for Curing Photocurable Compositions", assigned to the Assignee of this invention and accorded Ser. No. 182,643, filed Aug. 29, 1980.

This exposure may take place directly or through one or more surfaces of tooth material due to the significant transmittance of tooth material to visible light. Following exposure, the restorative material undergoes polymerization. During this process, and afterward, the materials of this invention exhibit color stability in accordance with A.D.A. Specification No. 27.

The following non-limiting examples further illustrate certain preferred embodiments of this invention.

EXAMPLE 1

Visible Light Curable Composition

A resinous blend may be formed from 13.57 g of the hexamethylene diisocyanate adduct of bis-GMA, 6.79 g of triethylene glycol dimethacrylate, 0.03 g of camphoroquinone and 0.1 g of N-methyldiethanolamine. To this resinous component blend can be added fillers and pigments comprising 78.02 g Raysorb T3000, a radiopaque silanated barium glass filler offered by the Kimble Company, 0.6 g of silanated alumina, 0.002 g yellow iron oxide, 0.005 g red iron oxide, 0.134 g of a dispersion of carbon black on barium glass and 0.75 g of Tullanox 300 which is a submicron silica available from the Tulco Co. The resulting filled blend is useful as a composite restorative and is curable by exposure to visible light. This dental composition is suitable for a wide range of dental restorative uses and is expected to pass A.D.A. Specification Number 27 for color stability.

EXAMPLE 2

Polymerized Dental Restorative

The composition of Example 1 can be exposed to visible radiation having wavelengths generally between about 4000 angstroms and about 5000 angstroms at an intensity of about 430 mw/cm$^2$. Exposure times of about 10 seconds are expected to result in depths of cure of about 2.5 mm. Longer exposures effect deeper and more complete cures. Exposure of about 30 seconds are expected to be sufficient for most restorative uses and exposure either through the composite or through tooth material will be effective in consummating polymerization. Teeth may be cleaned, etched and filled in the conventional way with the composition of Example 1. Irradiation of such preparations in various restorative configurations will yield well-formed, color stable, strong, and durable restored structures.

EXAMPLE 3

The hexamethylene diisocyanate (HMDI) adduct of bis-GMA is formulated in a diluent monomer, triethylene glycol dimethacrylate (TEGDMA), as follows. Bis-GMA, 38.12 g and 38.12 g of TEGDMA are blended with 11.86 g of HMDI in 11.86 g of TEGDMA and allowed to stand at room temperature for several weeks until the adduct has been substantially completely formed. Catalysis may, optionally, be used to speed the reaction rate. The resin blend, 20.36 g is formed comprising 10.18 g each of adduct and TEGDMA, mixed with 0.03 of camphoroquinone and 0.10 g of methyl diethanolamine. The resin blend is then added to 78.02 g of Raysorb T-3000, 0.6 g of silanated alumina, 0.002 g yellow iron oxide, 0.005 g red iron oxide, 0.134 g of carbon black on barium glass and 0.75 g Tullanex 300. The resulting filling blend is useful as a composite restorative and is curable by exposure to visible light. This dental composition is suitable for a wide range of dental restorative uses and passes A.D.A. Specification Number 27 for color stability.

EXAMPLE 4

The following composition is preferred for use in connection with one or more embodiments of the present invention:

| Resin Component | 24.00% |
|---|---|
| "Raysorb" T 3000 Silica | 76.00% |
| Modifiers and pigments | ≤1.00% |
| | 100.00% |

The "Resin Matrix" comprises:

| Hexamethylene diisocyanate adduct of 2,2-bis-[4-(2-hydroxy-3-methacryloxypropoxy)phenyl]propane | 49.65% |
|---|---|
| Triethylene glycol dimethacrylate | 49.65% |
| 2,6-di-tert-butyl-4-methylphenol | 0.05% |
| Camphoroquinone | 0.15% |
| Methyldiethanolamine | 0.50% |
| | 100.00% |

EXAMPLE 5

The composition of Examples 3 and 4 were exposed to visible light from a Dentsply Prisma ™ light unit at an intensity of about 430 mw/cm$^2$ for about 10 seconds to give depths of cure of about 2.5 mm. Exposures of 30 seconds are sufficient for most restorative uses. Irradiation through the tooth is effective in consummating polymerization.

What is claimed:

1. A process of restoring teeth comprising applying to a prepared tooth a dental restorative composition hardenable by irradiation with visible light comprising a blend of:
   a major proportion of an inorganic filler, and
   a minor proportion of a resin component having a viscosity of between about 5,000 and 70,000 centiposes at 25° C. comprising:
   a binder resin comprising bis-GMA reacted with a diisocyanate, a polymerizable acrylic diluent monomer present in an amount sufficient to dissolve said binder resin and a photosensitizing system comprising:

from about 0.05% to about 0.50% by weight of said resin component of a non-aromatic alpha diketone, and an amine reducing agent in an amount sufficient to improve the photocatalytic activity to visible light of said alpha diketone in said restorative composition, said inorganic filler and said resin component being present in relative amounts such that said restorative composition has a viscosity suitable for filling teeth, said composition being capable of passing American Dental Association Specification No. 27 for color stability, and exposing said composition to visible light to effect substantial polymerization thereof.

2. The process of claim 1 wherein said alpha diketone is either camphoroquinone or biacetyl.

3. The process of claim 1 wherein said alpha said alpha diketone is camphoroquinone.

4. The process of claims 2 wherein said amine is either an N-alkyldialkanolamine or a trialkanolamine.

5. The process of claim 1 wherein said light is composed predominantly of wavelengths between about 4000 angstroms and about 5000 angstroms.

6. A process of restoring teeth comprising applying to a prepared tooth a visible light hardenable dental restorative composition comprising:

a major proportion of an inorganic filler, and a minor proportion of a resin component having a viscosity of between about 5,000 and 70,000 centiposes at 25° C. comprising:

a binder resin comprising bis-GMA reacted with a diisocyanate, a polymerizable acrylic diluent monomer present in an amount sufficient to dissolve said binder resin, and a photosensitizing system comprising:

from about 0.05% to about 0.50% by weight of said component of a non-aromatic alpha diketone, and an amine reducing agent in an amount sufficient to improve the photocatalytic activity to visible light of said alpha diketone in said restorative composition, said inorganic filler and said resin component being present in relative amounts such that said restorative composition has a viscosity suitable for filling teeth, said composition being capable of passing American Dental Association Specification No. 27 for color stability, and irradiating said composition with visible light at least partially transmitted through at least one surface of the tooth.

7. The process of claim 6 wherein said alpha diketone is either camphoroquinone or biacetyl.

8. The process of claim 6 wherein said alpha diketone is camphoroquinone.

9. The process of claims 7 wherein said amine is either an N-alkyldialkanolamine or a trialkanolamine.

* * * * *